United States Patent [19]
Ebel et al.

[11] Patent Number: 5,994,562
[45] Date of Patent: Nov. 30, 1999

[54] PREPARATION OF N-ALKENYLCARBOXAMIDES

[75] Inventors: Klaus Ebel, Lampertheim; Matthias Eiermann, Limburgerhof; Thomas Narbeshuber; Eugen Gehrer, both of Ludwigshafen, all of Germany

[73] Assignee: BASF Aktiengesellschaft, Ludwigshafen, Germany

[21] Appl. No.: 09/229,996

[22] Filed: Jan. 14, 1999

[30] Foreign Application Priority Data

Jan. 16, 1998 [DE] Germany .......................... 198 01 549

[51] Int. Cl.$^6$ ...................... C07D 207/12; C07C 233/18; C07C 235/08
[52] U.S. Cl. .......................... 548/543; 548/552; 564/123; 564/189; 564/192; 564/193; 502/64; 502/77; 502/78; 502/79; 502/232; 502/243; 502/250; 502/411
[58] Field of Search ..................... 564/123, 189, 564/192, 193; 548/543, 552; 502/64, 77, 79, 232

[56] References Cited

U.S. PATENT DOCUMENTS

| | | | |
|---|---|---|---|
| 2,669,570 | 2/1954 | Scanizer | 260/326.5 |
| 3,821,245 | 6/1974 | Kanetaka et al. | 260/326.5 FN |
| 5,410,070 | 4/1995 | Franz et al. | 558/552 |
| 5,569,770 | 10/1996 | Kuo et al. | 548/543 |

FOREIGN PATENT DOCUMENTS

| | | |
|---|---|---|
| 232712 | 8/1987 | European Pat. Off. . |
| 608 690 | 8/1994 | European Pat. Off. . |
| 701 998 | 3/1996 | European Pat. Off. . |
| 2 135 211 | 1/1972 | Germany . |

OTHER PUBLICATIONS

Kirk–Othmer, Encyclopedia of Chemical Technology, Fourth Edition, vol. 5, "Catalysis by Metal Oxides and Zeolites," pp. 356–363, 1993.

Kirk–Othmer, Encyclopedia of Chemical Technology, Fourth Edition, vol. 16, "Molecular Sieves," pp. 888–897, 1995.

*Primary Examiner*—Johann Richter
*Assistant Examiner*—Jane C. Osweeki
*Attorney, Agent, or Firm*—Keil & Weinkauf

[57] ABSTRACT

In a process for preparing N-alkenylcarboxamides by dehydration of N-(2-hydroxyalkyl)carboxamides and/or diethers thereof in the presence of a catalyst, molecular sieves, in particular zeolites, are used as catalyst.

7 Claims, No Drawings

PREPARATION OF N-ALKENYLCARBOXAMIDES

The present invention relates to a process for preparing N-alkenylcarboxamides by dehydration of N-(2-hydroxyalkyl)carboxamides and/or diethers thereof in the presence of a catalyst.

N-Alkenylcarboxamides are widely used in industrial products. For example, N-vinylpyrrolidone (NVP) is used for preparing poly(N-vinylpyrrolidone) (PVP). PVP is used, for example, as an additive in hairsprays, as PVP-iodine complex in ointments, as a component of melt-extruded pellets or as a clarifier in the brewing of beer. NVP can be prepared by the Reppe process by vinylation of pyrrolidone using acetylene. However, the industrial handling of acetylene, which is also used for preparing the pyrrolidone used, is difficult and associated with risks because of its reactivity.

An alternative route to NVP is dehydration of N-(2-hydroxyethyl)pyrrolidone (HEP) which can be prepared from the readily available components butyrolactone and monoethanolamine. Many processes of this type have been described.

DE-A-2 135 211 describes a process for preparing N-vinylpyrrolidone using an oxide of zirconium, thorium, cerium, zinc, chromium or zinc/chromium as catalyst.

In U.S. Pat. No. 2,669,570, activated aluminum oxide is used as dehydration catalyst.

In EP-A-0 608 690, use is made of silicon dioxide treated with phosphoric acid or diatomaceous earth treated with lanthanum nitrate and phosphate.

In EP-A-0 701 998, silicon dioxide doped with an alkali metal salt is used.

Some of the abovementioned processes have to be carried out under reduced pressure or they have selectivities which are too low.

It is an object of the present invention to provide a process for preparing N-alkenylcarboxamides by dehydration of N-(2-hydroxyalkyl)carboxamides and/or diethers thereof in the presence of a catalyst, which process makes it possible to achieve high conversions and selectivities under atmospheric pressure, particularly in the synthesis of NVP from HEP.

We have found that this object is achieved by use of molecular sieves, in particular zeolites, as catalyst in the above reaction.

Catalysts based on molecular sieves are particularly suitable for the highly selective preparation of NVP from HEP when the modulus, i.e. the ratio of silicon, calculated as silicon dioxide, to aluminum, calculated as aluminum oxide, is at least 140, particularly preferably at least 150, in particular at least 200, especially at least 250.

At a low modulus, i.e. a high concentration of acid centers, the NVP selectivity is low because of the dominant formation of the ether produced formally by elimination of water from 2 molecules of HEP. However, this ether can itself serve as starting material for preparing NVP. It can therefore be recirculated and does not contribute to a reduction in yield in a continuous synthesis. Pyrrolidone can be formed as a non-recirculatable and therefore largely undesirable by-product in a continuous process.

At a high modulus, i.e. a low concentration of acid centers, high selectivity and yield in respect of NVP are observed at the same time as a low tendency to form pyrrolidone. When the molecular sieves, in particular zeolites, are doped with at least one alkali metal compound or alkaline earth metal compound, the ether formation is further reduced. Preference is given to carrying out doping with an alkali metal, preferably using sodium and/or potassium salts. In this case, virtually none of the diether of HEP is found. In addition, the pyrrolidone formation can be greatly reduced and the conversions are high.

Preference is given to using zeolites of the type ZSM5 (MFI), Y (FAU), LDK10 or silicalite as catalyst. Examples are the zeolite catalysts MFI, MOR and FAU.

The catalysts used according to the present invention are preferably used as shaped bodies in a static or agitated catalyst bed. The shaped bodies can be, for example, extrudates or spheres. Auxiliaries such as Pural® from Condea, Walocel® from Wolf/Walsrode, potato starch or Aerosil® from Degussa, preferably Walocel and Aerosil, can be used in the production of the shaped bodies. The proportion of auxiliaries in the shaped body can be from 0 to 60% by weight, preferably from 10 to 40% by weight.

The dehydration is preferably carried out in the gas phase, if desired in the presence of a carrier gas. Here, preference is given to using a static or an agitated catalyst bed, particularly preferably a static catalyst bed.

The dehydration is preferably carried out continuously.

The reaction is preferably carried out at from 200 to 450° C. At temperatures which are too high, undesirable by-products are formed, while if the temperature is too low, the conversions are uneconomically low. Preference is given to temperatures within a range from 200 to 400° C.

As carrier gas, it is possible to use, for example, argon or nitrogen, preferably nitrogen. The pressure during the reaction is preferably from 0.05 to 5 bar. In particular, the reaction is carried out at ambient pressure (atmospheric pressure). The proportion of inert gas in the reactor feed can be from 0 to 90 mol %, preferably from 50 to 85 mol %. The space velocity over the catalyst, given as the amount of N-(2-hydroxyalkyl)carboxamide per unit volume of catalyst and per unit time, can be from 0.5 to 30 mol/l h, preferably from 1 to 15 mol/l h. If the space velocity is too low, only poor space-time yields are obtained, while space velocities which are too high result in only unsatisfactory conversions, thus increasing the cost of the subsequent work-up.

N-(2-Hydroxyalkyl)carboxamides which have not been dehydrated and/or diethers thereof formed as by-products are preferably recirculated to the dehydration in the continuous process.

As N-(2-hydroxyalkyl)carboxamides, preference is given to using the $C_2$–$C_{12}$-alkyl compounds, particularly preferably $C_2$–$C_6$-alkyl compounds, in particular (2-hydroxyethyl)pyrrolidone or the diether thereof.

The invention is illustrated by the examples below.

Preparation of the Catalysts

Catalyst A: 500 g of LDK10 (USY, Uetikon, mod. 5.2) are compounded with 35 g of Walocel® from Wolf/Walsrode and 470 ml of water for 1 hour in a kneader and extruded at a pressing pressure of 80 bar to form 2 mm extrudates. The extrudates are dried at 110° C. for 16 hours and calcined at 500° C. for 16 hours.

Catalyst B: 160 g of H-ZSM-5 (VAW, mod. 28.6) are compounded with 40 g of Aerosil® 200 from Degussa, 5% of potato starch and 185 g of water for 45 minutes in a kneader, then extruded at a pressing pressure of 90 bar to form 2 mm extrudates, dried at 110° C. for 16 hours and calcined at 500° C. for 16 hours.

Catalyst C: 120 g of H-ZSM-5 (Uetikon, mod. 57.4) are compounded with 120 g of Aerosil® 200, 5% of potato starch and 200 g of water for 45 minutes in a kneader, then extruded at a pressing pressure of 110 bar to form 2 mm extrudates, dried at 110° C. for 16 hours and calcined at 500° C. for 16 hours.

Catalyst D: 700 g of $NH_4$-ZSM-5 (Conteka, mod. 140) are compounded with 7% of Walocel®, 330 g of water and 2% of $NH_4OH$ solution for 45 minutes in a kneader, then extrudated at a pressing pressure of 90 bar to form 2 mm extrudates, dried at 110° C. for 16 hours and calcined at 500° C. for 16 hours.

Catalyst E: 800 g of Na-Y zeolite (BASF, mod. 3.3) are subjected to ion exchange with a 20% strength $NH_4OH$ solution (ratio 1:5) for 2 hours at 80° C. while stirring. The product is washed with water until free of nitrate, dried at 110° C. and calcined at 590° C. for 2 hours. This procedure is repeated three times. 610 g of the product obtained in this way are stirred into 2N $HNO_3$ (ratio 1:6) for 3 hours at 95° C., washed with hot water, dried at 110° C. and calcined at 530° C. for 4 hours. The product obtained in this way is, according to the XRD pattern, a zeolite of the faujasite type. Elemental analysis gave a modulus of 149. 200 g of this product are compounded with 8% of Walocel® from Wolf/Walsrode and 220 g of water for 45 minutes in a kneader, extruded at a pressing pressure of 100 bar to form 2 mm extrudates, dried at 110° C. and calcined at 500° C. for 16 hours.

Catalyst F: 240 g of H-ZSM-5 (BASF, mod. 386) are compounded with Pural® from Condea, 2% of formic acid and 180 g of water for 45 minutes in a kneader, then extruded at a pressing pressure of 70 bar to form 2 mm extrudates, dried at 110° C. for 16 hours and calcined at 500° C. for 16 hours.

Catalyst G: 100 ml of extrudates of catalyst E are stirred at 80° C. with a solution of 30 g of potassium acetate in 300 ml of water for 24 hours. The product is filtered off, washed with hot water, dried at 110° C. and calcined at 500° C. for 16 hours.

Catalyst H: 240 g of borosilicalite (BASF, mod. 340) are compounded with 105 g of Aerosil® 200, 5% of potato starch and 200 g of water for 45 minutes in a kneader, then extruded at a pressing pressure of 70 bar to form 2 mm extrudates, dried at 110° C. for 16 hours and calcined at 500° C. for 16 hours. 30 g of the product obtained in this way are impregnated with a solution of 3 g of potassium carbonate and 18 g of water, dried at 60° C. and at 110° C. and calcined at 540° C. for 2 hours.

Catalyst J: 240 g of ZSM-5 (BASF, mod. 386) are compounded with 160 g of Pural® (ratio 60:40), 2% of formic acid and 180 g of water for 45 minutes in a kneader, extruded at a pressing pressure of 70 bar to form 2 mm extrudates, dried at 110° C. and calcined at 500° C. for 16 hours. 100 ml of the product obtained in this way are treated at 80° C. with a solution of 29.44 g of potassium acetate and 300 ml of water for 24 hours, the resulting product is dried at 110° C. and calcined at 500° C. for 16 hours.

Dehydration

General experimental procedure

The experiments were carried out in an electrically heated, vertical tube reactor having an internal diameter of 20 mm, into which the catalyst extrudates (30 ml) were introduced as a bed. A bed (50 ml) of quartz rings located above the catalyst zone served as vaporization zone for the liquid starting compound fed in from above. The temperature in the catalyst zone was measured and regulated by means of a centrally positioned, axially movable thermocouple. The measuring tip of the thermocouple was located in the middle of the catalyst bed during operation of the apparatus. As carrier gas stream, high-purity nitrogen was separately metered in from above. The product stream was taken off from the reactor at the bottom, completely condensed in a coil condenser and analyzed by means of gas chromatography using an internal standard. The results reported were determined from balances over a number of hours after steady-state operation had been reached. The standard conditions were: 350° C., atmospheric pressure, space velocity of HEP: 2.3 mol/l h, space velocity of nitrogen: 10 mol/l h.

EXAMPLES 1 TO 6 (undoped catalysts)

| Ex. | Cat. | Cat./modulus | C(HEP) | S(NVP) | S(pyr-rolidone) | S(HEP$_2$O) |
|---|---|---|---|---|---|---|
| 1 | A | US-Y/5.3 | 79% | 9% | 9% | 71% |
| 2 | B | H-ZSM-5/28 | 53% | 11% | 6% | 61% |
| 3 | C | H-ZSM-5/57 | 58% | 18% | 7% | 58% |
| 4 | D | H-ZSM-5/140 | 53% | 31% | 29% | 22% |
| 5 | E | H-Y/149 | 67% | 41% | 13% | 18% |
| 6 | G | H-ZSM-5/385 | 88% | 85% | 2% | 10% |

EXAMPLES 7 AND 8 (potassium doping)

| Ex. | Cat. | Cat./modulus | C(HEP) | S(NVP) | S(pyr-rolidone) | S(di-ether) |
|---|---|---|---|---|---|---|
| 7 | G | K-USY/3.3 | 83% | 93% | 2% | 0% |
| 8 | H | K-ZSM-5/340 | 93% | 96% | 4% | 0% |

EXAMPLES 9 TO 11 (alteration of space velocity over the catalyst)

| Ex. | Cat. | Cat./modulus | Space velocity | C(HEP) | S(NVP) | S(pyr-rolidone) | S(di-ether) |
|---|---|---|---|---|---|---|---|
| 9 | H | K-ZSM-5/340 | 2.3 mol/l h | 100% | 92% | 8% | 0% |
| 10 | H | K-ZSM-5/340 | 7.3 mol/l h | 90% | 90% | 2% | 0% |
| 11 | H | K-ZSM-5/340 | 14.6 mol/l h | 59% | 92% | 1% | 1% |

As can be seen from the results of Examples 9 to 11, the selectivity in respect of NVP is virtually constant over a wide range of space velocities.

EXAMPLE 12 (dehydration of the diether)

| Ex. | Cat. | Cat./modulus | Space velocity | C(di-ether) | S(NVP) | S(HEP) | S(pyr-rolidone) |
|---|---|---|---|---|---|---|---|
| 12 | J | K-ZSM-5-386 | 1.2 mol/l h | 49% | 24% | 15% | 14% |

The catalyst systems described are suitable for converting the diether into NVP, corresponding to recirculation of the diether in a continuous process, as can be seen from the results of Example 12. This example was carried out under standard conditions with the exception of the temperature which was 400° C.

We claim:

1. A process for preparing N-alkenylcarboxamides by dehydration of N-(2-hydroxyalkyl)carboxamides or diethers thereof or their mixtures in the presence of a zeolite catalyst wherein the dehydration is carried out continuously and wherein N-(2-hydroxyalkyl)carboxamides which have not been dehydrated and/or diethers thereof formed as byproducts are recirculated to the dehydration.

2. A process as claimed in claim 1, wherein the modulus of the molecular sieve is at least 140.

3. A process as claimed in claim 1, wherein the catalyst used is a zeolite selected from the group consisting of ZSM5, Y, LDK10 or silicalite.

4. A process as claimed of claim 1, wherein the catalyst is doped with at least one alkali metal compound or alkaline earth metal compound.

5. A process as claimed in claim 1, wherein the catalyst is used as shaped bodies in a static or agitated catalyst bed.

6. A process as claimed in claim 1, wherein the dehydration is carried out in the gas phase, if desired in the presence of a carrier gas.

7. A process as claimed in claim 1, wherein (2-hydroxyethyl)pyrrolidone or the diether thereof is dehydrated.

* * * * *